United States Patent
Dewey et al.

(10) Patent No.: US 8,100,945 B2
(45) Date of Patent: Jan. 24, 2012

(54) INTERVERTEBRAL PROSTHETIC DEVICE FOR SPINAL STABILIZATION AND METHOD OF IMPLANTING SAME

(75) Inventors: Jonathan M. Dewey, Raleigh, NC (US); Fred J. Molz, IV, Birmingham, AL (US); Aurelien Bruneau, Jacksonville, FL (US); Eric C. Lange, Pleasanton, CA (US); Matthew M. Morrison, Cordova, TN (US); Thomas A. Carls, Memphis, TN (US); Kent M. Anderson, Sunnyvale, CA (US); Jean M. Taylor, Cannes (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 163 days.

(21) Appl. No.: 12/573,772

(22) Filed: Oct. 5, 2009

(65) Prior Publication Data

US 2010/0023059 A1    Jan. 28, 2010

Related U.S. Application Data

(63) Continuation of application No. 11/333,919, filed on Jan. 18, 2006, now abandoned.

(51) Int. Cl.
*A61B 17/70* (2006.01)

(52) U.S. Cl. ........................ 606/249

(58) Field of Classification Search ............. 606/60, 606/246, 248, 249, 257, 276, 277
See application file for complete search history.

(56) References Cited

U.S. PATENT DOCUMENTS

| | | | | |
|---|---|---|---|---|
| 5,645,599 A * | 7/1997 | Samani | ............. | 623/17.16 |
| 6,626,944 B1 * | 9/2003 | Taylor | ............. | 623/17.16 |
| 7,238,204 B2 * | 7/2007 | Le Couedic et al. | ... | 623/17.11 |
| 7,377,942 B2 * | 5/2008 | Berry | ............. | 623/17.11 |
| 7,682,376 B2 * | 3/2010 | Trieu | ............. | 606/248 |
| 7,691,130 B2 * | 4/2010 | Bruneau et al. | ... | 606/249 |
| 7,763,073 B2 * | 7/2010 | Hawkins et al. | ... | 623/17.11 |
| 7,846,209 B2 * | 12/2010 | Arnin et al. | ... | 623/17.16 |
| 7,879,104 B2 * | 2/2011 | Dewey et al. | ... | 623/17.16 |
| 2004/0106995 A1 * | 6/2004 | Le Couedic et al. | ... | 623/17.11 |
| 2005/0261768 A1 * | 11/2005 | Trieu | ............. | 623/17.11 |
| 2007/0233076 A1 * | 10/2007 | Trieu | ............. | 606/61 |

\* cited by examiner

*Primary Examiner* — Eduardo C Robert
*Assistant Examiner* — Ellen C Hammond

(57) ABSTRACT

A prosthetic device for insertion in a spinal column includes a first, second, and third members. The first member includes an inferiorly extending tab and is of a relatively flexible material. The second member includes a superiorly extending tab and is of a relatively flexible material. The third member defines a superior opening for receiving the inferiorly extending tab and an inferior opening for receiving the superiorly extending tab and is of a relatively stiff material. The device also includes a means for providing a rigid connection of the third member to a vertebra.

5 Claims, 4 Drawing Sheets ical device for stabilizing the human spine, and a method of implanting same.
INTERVERTEBRAL PROSTHETIC DEVICE FOR SPINAL STABILIZATION AND METHOD OF IMPLANTING SAME This application is a continuation of application Ser. No. 11/333,919, filed Jan. 18, 2006, the disclosure of which is incorporated herein by reference.

BACKGROUND

The present invention relates to an intervertebral prosthetic device for stabilizing the human spine, and a method of implanting same.

Spinal discs that extend between adjacent vertebrae in vertebral columns of the human body provide critical support between the adjacent vertebrae while permitting multiple degrees of motion.

These discs can rupture, degenerate, and/or protrude by injury, degradation, disease, or the like to such a degree that the intervertebral space between adjacent vertebrae collapses as the disc loses at least a part of its support function, which can cause impingement of the nerve roots and severe pain.

In these cases, intervertebral prosthetic devices have been designed that can be implanted between the adjacent vertebrae, both anterior and posterior of the column and are supported by the respective spinous processes of the vertebrae to prevent the collapse of the intervertebral space between the adjacent vertebrae and provide motion stabilization of the spine. Many of these devices are supported between the spinous processes of the adjacent vertebrae.

In some situations it is often necessary to remove the laminae and the spinous process from at least one of the adjacent vertebrae to get proper decompression. In other situations, the defective disc is removed and two vertebral segments are fused together to stop any motion between the segments and thus relieve the pain. When two adjacent vertebrae are fused, the laminae and the spinous process of at least one vertebra are no longer needed and are therefore often removed.

However, in both of the above situations involving removal of a spinous process, it would be impossible to implant an intervertebral prosthetic device of the above type since the device requires support from both processes.

SUMMARY

According to an embodiment of the invention, an intervertebral prosthetic device is provided that is implantable between two adjacent vertebrae, at least one of which is void of a spinous process, to provide motion stabilization.

Various embodiments of the invention may possess one or more of the above features and advantages, or provide one or more solutions to the above problems existing in the prior art.

DETAILED DESCRIPTION

Figure 1:
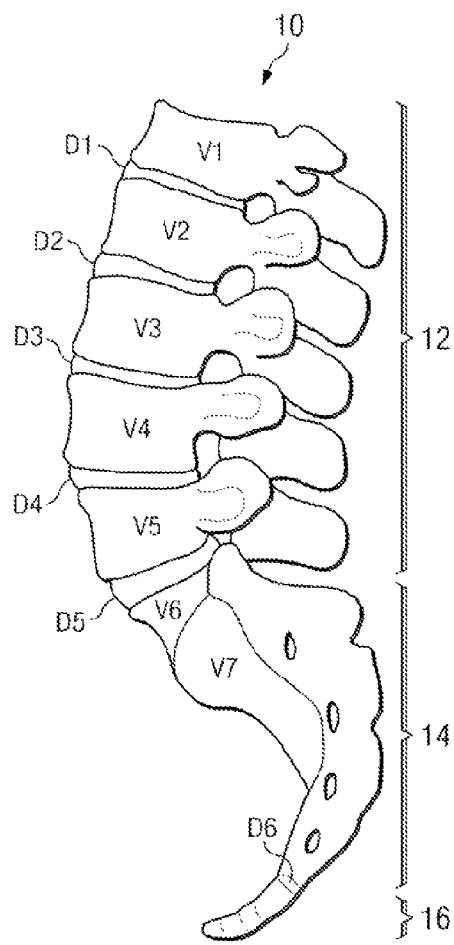
FIG. 1 is a side elevational view of an adult human vertebral column.
Figure 2:
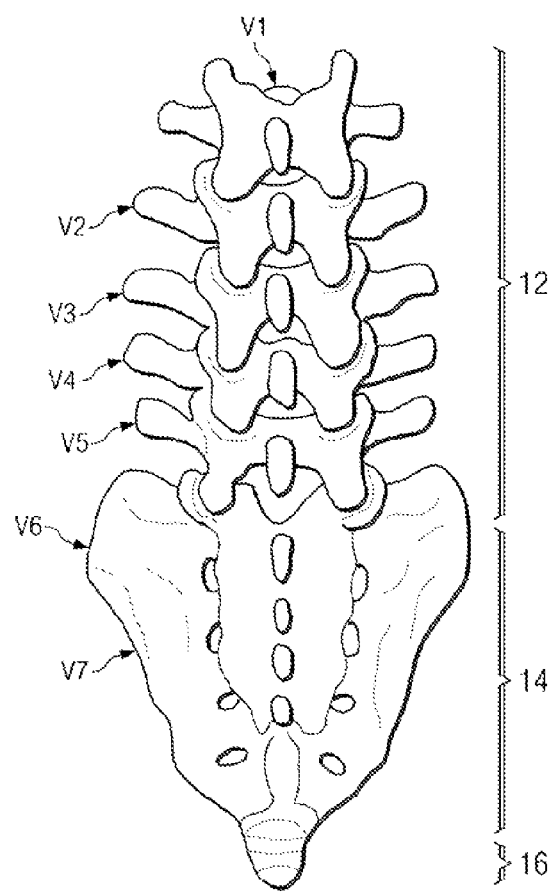
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the sacrum 14, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebrae V6 separated from the vertebrae V5 by a disc D5. The other four fused vertebrae of the sacrum 14 are referred to collectively as V7. A disc D6 separates the vertebrae V6 from the coccyx 16 which includes four fused vertebrae (not referenced).

Figure 3:
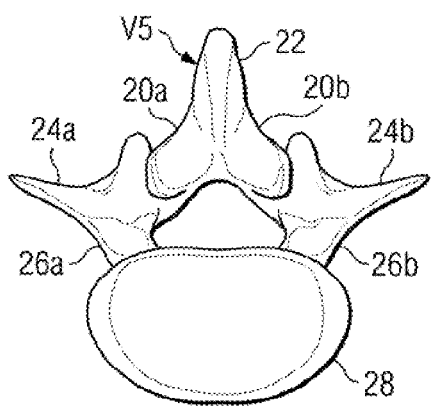
FIG. 3 is an enlarged, front elevational view of one of the vertebrae of the column of FIGS. 1 and 2.

With reference to FIG. 3, the vertebra V5 includes two laminae 20a and 20b extending to either side (as viewed in FIG. 2) of a spinous process 22 that projects posteriorly from the juncture of the two laminae. Two transverse processes 24a and 24b extend laterally from the laminae 20a and 20b, respectively, and two pedicles 26a and 26b extend inferiorly from the processes 24a and 24b to a vertebral body 28. Since the other vertebrae V1-V3 are similar to the vertebra V5 they will not be described in detail. Also, V4 is similar to V5 with the exception that the spinous process 22 of V4 has been removed for one or both of the reasons set forth below.

Figure 4:
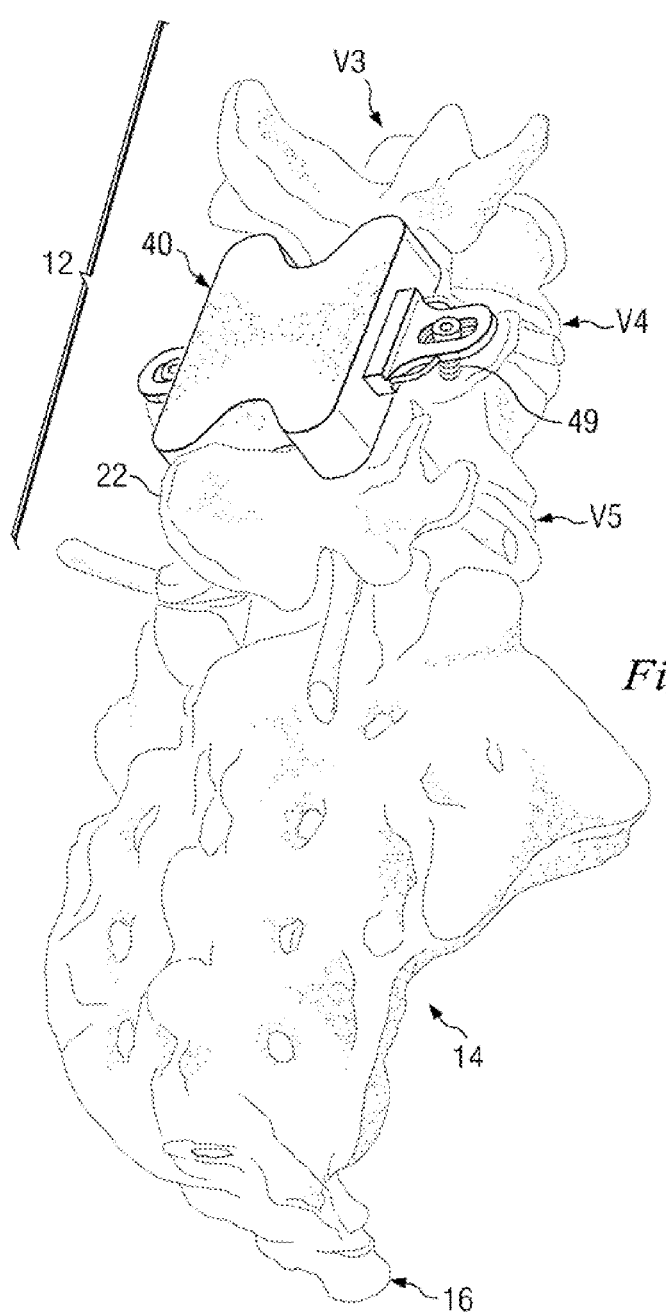
FIG. 4 is an enlarged, partial, isometric view of a portion of the column of FIGS. 1 and 2, including the lower three vertebrae of the column, and depicting an intervertebral prosthetic device according to an embodiment of the invention implanted between two adjacent vertebrae.

Referring to FIG. 4, it will be assumed that, for one or more of the reasons set forth above, the vertebrae V4 and V5 are not being adequately supported by the disc D4 and that it is therefore necessary to provide supplemental support and stabilization of these vertebrae. As stated above, it will also be assumed that the spinous process 22 of V4 has been removed.

Figure 5:
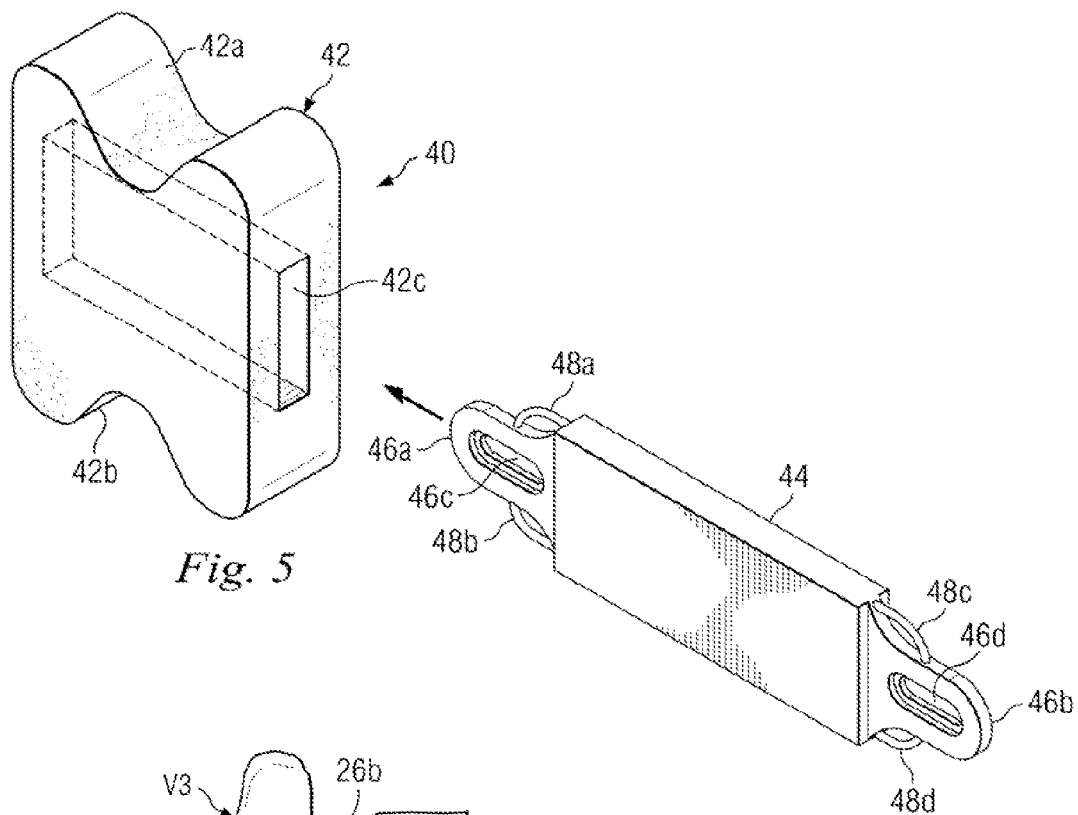
FIG. 5 is an enlarged, isometric, exploded view of the prosthetic device of FIG. 4.

An intervertebral disc prosthetic device 40 according to an embodiment of the invention is provided which is adapted to be implanted between the spinous processes 22 of the vertebrae V3 and V5. The prosthetic device 40 is shown in detail in FIGS. 5 and 6 and includes a spacer 42 which is substantially rectangular in shape with the exception that two curved notches 42a and 42b are formed in the respective end portions thereof. A laterally extending channel 42c, having a substantially rectangular cross section, extends through the entire width of the spacer 42 approximately midway between the notches 42a and 42b.

An insert 44 is provided that is dimensioned so as to extend in the channel 42c with minimum clearance. Tabs 46a and 46b extend out from the respective ends of the insert 44 and elongated openings 46c and 46d extend through the respective tabs. The length of the insert 44 substantially corresponds to the length of the channel 42c so that when the insert is inserted in the channel, the tabs 46a and 46b project outwardly from the channel.

Two protrusions 48a and 48b extend from the sides of the tab 46a and two protrusions 48c and 48d extend from the sides of the tab 46b. The protrusions are for the purpose of receiving tethers, or the like, to tether the device 40 to the vertebrae V4 and/or V5.

Since the spinous process of the vertebra V4 has been removed, the device 40 is implanted between the spinous process 22 of the vertebra V3 and the spinous process 22 of the vertebra V5. In the implanted position shown in FIGS. 4 and 6, the spinous process 22 of the vertebra V3 extends in the notch 42a of the spacer 42, and the spinous process 22 of the vertebra V5 extends in the notch 42b. The dimensions of the device 40 are such that, when it is implanted in this manner, the elongated openings 46c and 46d extend over the pedicles 26a and 26b (FIG. 3) of the vertebra V4.

Figure 6:
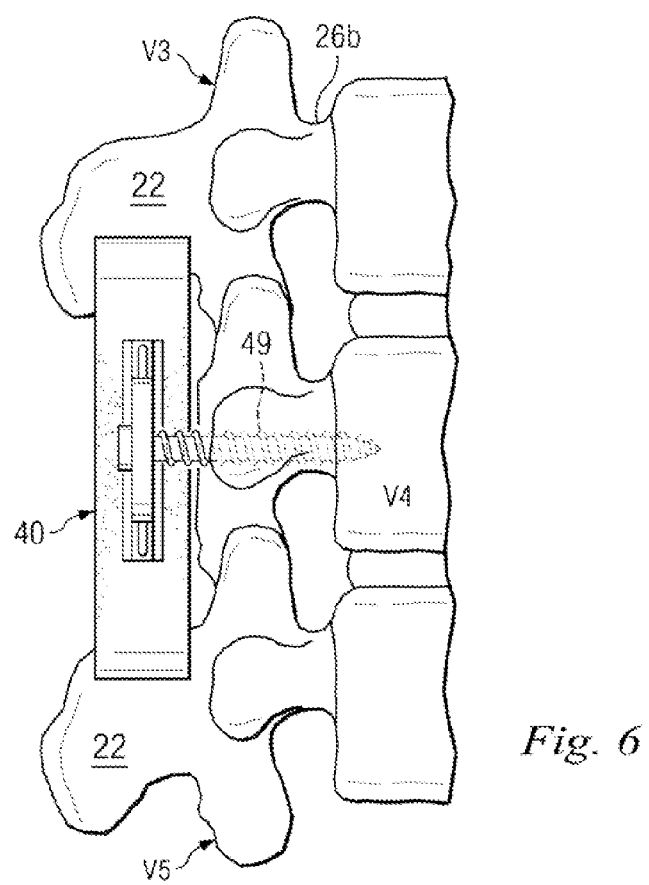
FIG. 6 is a cross-sectional view of the implanted device of FIGS. 4 and 5.

Then, two screws, one of which is referred to by the reference numeral 49 in FIGS. 4 and 6, are inserted through the elongated openings 42c and 42d, respectively, of the spacer 42. Torque is applied to the screws 49 so that they are driven into the pedicles 26a and 26b of the vertebra V4. The elongated openings 46c and 46d in the tabs 46a and 46b, respectively, enable the screws 49 to be adjusted laterally and to be angled towards the pedicles 26a and 26b as necessary so that they can be driven into the pedicles.

Although not shown in the drawing, tethers can be tied between the protrusions 48a-48d and the vertebrae V3, V4, and/or V5 to provide additional support and resistance.

As examples of the materials making up the spacer 42 and the insert 44, the spacer can be of a relatively soft material, such as soft plastic, including silicone, while the insert can be of a relatively stiff material, such as hard plastic or rubber. In the latter context, the surgeon could be provided with several inserts 44 that vary in stiffness, and once the condition of the vertebrae V4 and V5 (FIG. 4), and therefore the desired stiffness, is determined, the proper insert 44 can be selected.

When the device 40 is implanted in the manner discussed above, the relatively flexible, soft spacer 42 provides non-rigid connections to the vertebrae V3 and V5 that readily conforms to the spinous processes 22 of the vertebrae V3 and V5 and provides excellent shock absorption, while the insert 44 adds stiffness, compressive strength and durability, and the screws 49 provide a rigid connection to the vertebra V4.

Figure 7:
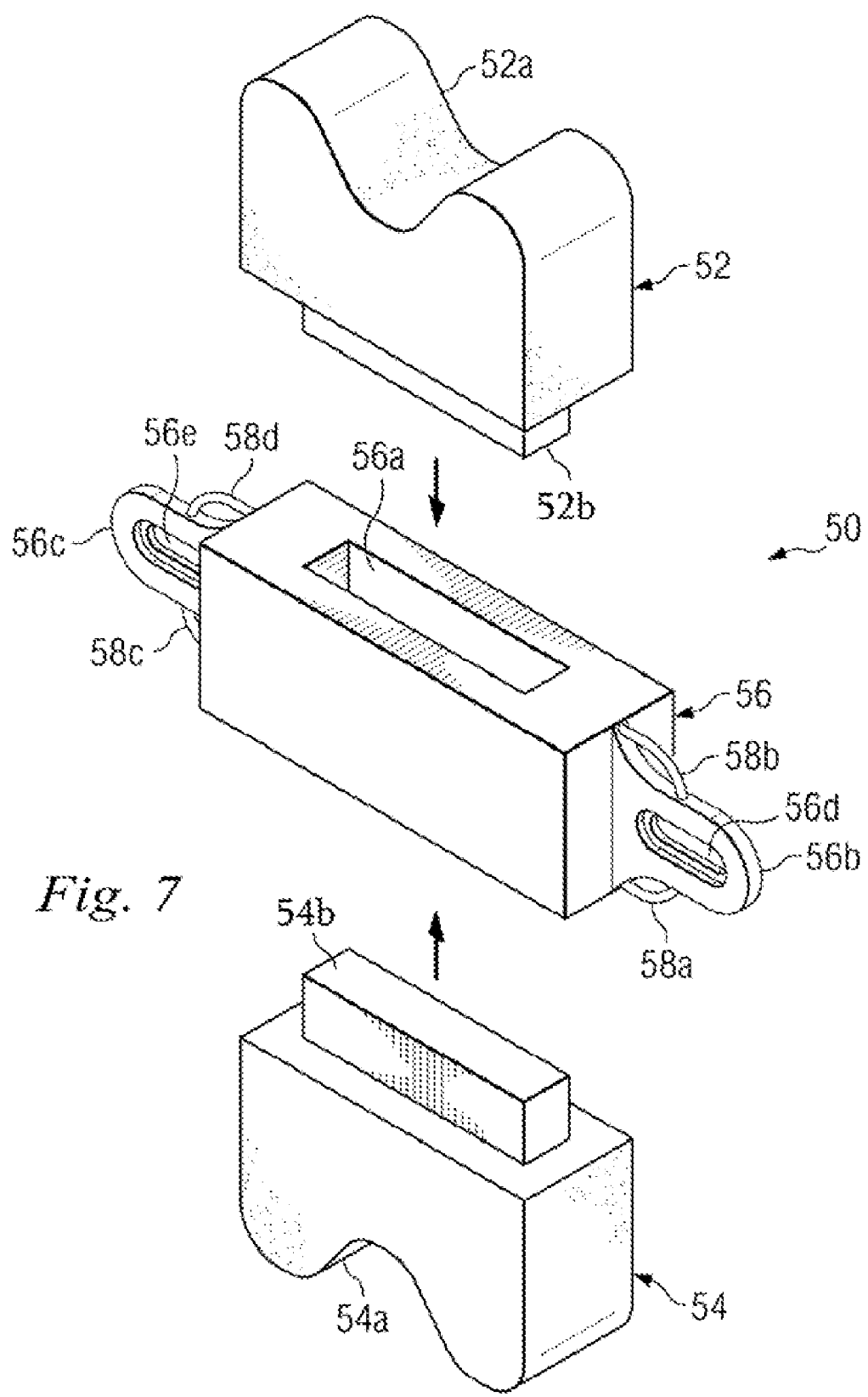
FIG. 7 is an enlarged, isometric, exploded view of an alternate embodiment of the prosthetic device of FIG. 5.

A prosthetic device 50 according to another embodiment is shown in detail in FIG. 7 and includes a spacer 52 which is substantially rectangular in shape with the exception that a curved notch 52a, is formed in one end portion. A tab 52b projects from the other end of the spacer 52 for reasons to be described.

A spacer 54 is also provided which is substantially rectangular in shape with the exception that a curved notch 54a is formed in one end portion and a tab 54b projects from the other end of the spacer 54.

A connector 56 is designed to fit over the tabs 52b and 54b of the spacers 52 and 54, respectively, to connect them. To this end, the connector 56 has a through opening 56a with a cross section slightly greater than the cross sections of the tabs 52b and 54b.

Two tabs 56c and 56b extend out from the respective ends of the connector 56, and elongated openings 56e and 56d extend through the respective tabs for receiving screws, for reasons to be described.

Two protrusions 58a and 58b extend from the sides of the tab 56b and two protrusions 58c and 58d extend from the sides of the tab 56c. The protrusions are for the purpose of receiving tethers, or the like, to tether the device 50 to the vertebrae V4 and/or V5.

To connect the spacers 52 and 54, their respective tabs 52b and 54b are inserted into the opening 56a of the connector 56 from opposite ends of the opening until the corresponding shoulders of the spacers 52 and 54 engage the corresponding ends of the connector 56. The spacers 52 and 54 and the connector are sized so that the tabs 52b and 54b engage the inner wall of the connector 56 in a friction fit so as to retain the spacers 52 and 54 in the connector.

Since the spinous process of the vertebra V4 has been removed, the device 50 is implanted between the spinous process 22 of the vertebra V3 and the spinous process 22 of the vertebra V5. In the implanted position, the spinous process 22 of the vertebra V3 extends in the notch 52a of the spacer 42, and the spinous process 22 of the vertebra V5 extends in the notch 54a. The dimensions of the device 50 are such that, when it is implanted in this manner, the elongated openings 56d and 56e extend over the pedicles 26a and 26b (FIG. 3) of the vertebra V4.

Although not shown in the drawing, tethers can be tied between the protrusions 58a-58d and the vertebrae V3, V4, and/or V5 to provide additional support and resistance.

The spacers 52 and 54 could be fabricated from a relatively soft material, such as soft plastic, including silicone, while the connector 56 could be fabricated from a relatively stiff material, such as hard plastic or rubber. In the latter context, the surgeon could be provided with several connectors 56 that vary in stiffness. Thus, once the surgeon ascertains the condition of the vertebrae V3, V4, and V5 (FIG. 3) and determines the particular stiffness that is needed, the proper connector 56 can be selected.

Thus, when the device 50 is implanted between the spinous processes 22 of the vertebrae V3 and V5 in the manner discussed above, the relatively flexible, soft spacers 52 and 54 provide a non-rigid connection to the vertebrae V3 and V5 that readily conforms to the spinous processes 22 of the vertebrae V3 and V5, and provides excellent shock absorption. Also, the connector 56 adds stiffness, compressive strength and durability, and the screws 49 provide a rigid connection to the vertebra V4.

It is understood that other variations may be made in the foregoing without departing from the invention and examples of some variations are as follows:

Any conventional substance that promotes bone growth, such as HA coating, BMP, or the like, can be incorporated in the prosthetic device of the above embodiments.

One or more of the components of the above devices may have through holes formed therein to improve integration of the bone growth.

The surfaces of the body member defining the notch can be treated, such as by providing teeth, ridges, knurling, etc., to better grip the spinous processes and the adapters.

The body member can be fabricated of a permanently deformable material thus providing a clamping action against the spinous process.

The spacers and associated components of one or more of the above embodiments may vary in shape, size, composition, and physical properties.

Through openings can be provided through one or more components of each of the above prosthetic devices to receive tethers for attaching the devices to a vertebra or to a spinous process.

The prosthetic device of each of the above embodiments can be placed between two vertebrae in the vertebral column 10 other than the ones described above.

The prosthetic device of each of the above embodiments can be fabricated from materials other than those described above.

The relative stiff components described above could be made of a resorbable material so that their stiffness would change over time.

The prosthesis of the above embodiments can be implanted between body portions other than vertebrae.

In the embodiment of FIG. 7, the spacers 52 and 54 can be fabricated from a relatively stiff material and the connector 56 from a relatively soft, flexible material.

The prostheses of the above embodiments can be inserted between two vertebrae following a discectemy in which a disc between the adjacent vertebrae is removed, or a corpectomy in which at least one vertebra is removed.

The spatial references made above, such as "under", "over", "between", "flexible, soft", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. A prosthetic device for insertion in a spinal column, the device comprising:
    a first member of a relatively flexible material, the first member having a superior end having a first notch formed therein sized to cradle a spinous process of an upper vertebra;
    a second member of a relatively flexible material, the second member having an inferior end having a second notch formed therein sized to cradle a spinous process of a lower vertebra;
    a third member of a relatively stiff material and having a greater stiffness than the first member and the second member, the third member being located between the first member and the second member;
    first protrusion extending outwardly from a first lateral side of the third member and a second protrusion extending outwardly from a second opposite lateral side of the third member, the first and second protrusions configured to provide a rigid connection of the third member to a vertebra located between the upper vertebra and the lower vertebra;
    wherein a theoretical plane extends through the first, second, and third members, and extends through a first intersection between the first protrusion and the third member a second intersection between the second protrusion and the third member.

2. The device of claim 1 wherein the means for providing the rigid connection comprises two screws extending through openings defined at lateral end portions of the third member.

3. The device of claim 1 further comprising means on the third member for receiving a cable to tether the device to at least one of the vertebrae.

4. The device of claim 1 wherein the superior end of the first member and the inferior end of the second member are spaced a sufficient distance apart to cradle the spinous processes of the upper and lower vertebrae when the upper and lower vertebrae are not adjacent.

5. The device of claim 1 wherein the first member has an inferior end defining an inferiorly extending tab, the second member has a superior end defining a superiorly extending tab, and the third member defines a superior opening for receiving the inferiorly extending tab of the first member and an inferior opening for receiving the superiorly extending tab of the second member.

* * * * *